United States Patent
Akervall

(10) Patent No.: US 6,341,608 B1
(45) Date of Patent: Jan. 29, 2002

(54) METHOD FOR RESECTION OF TUMORS

(76) Inventor: Jan Akervall, Helgonavägen 21, 223 63 Lund (SE)

(*) Notice: Subject to any disclaimer, the term of this patent is extended or adjusted under 35 U.S.C. 154(b) by 0 days.

(21) Appl. No.: 09/395,469

(22) Filed: Sep. 14, 1999

(51) Int. Cl.⁷ .............................................. A61B 19/00

(52) U.S. Cl. ...................................................... 128/898

(58) Field of Search .......................... 128/898; 424/422, 424/423, 424, 426, 428; 435/177; 427/213.35, 213.3, 213.32

(56) References Cited

U.S. PATENT DOCUMENTS

| | | | | |
|---|---|---|---|---|
| 5,573,934 A | * | 11/1996 | Hubbell et al. | 435/177 |
| 5,843,156 A | * | 12/1998 | Slepian et al. | 623/1 |
| 6,110,484 A | * | 8/2000 | Sierra | 424/426 |

* cited by examiner

*Primary Examiner*—David J. Isabella
(74) *Attorney, Agent, or Firm*—Baker & McKenzie

(57) ABSTRACT

According to the present invention, a tumor to be surgically removed is coated with a tissue adhesive composition before resection thereof. Thus, the tissue adhesive composition functions as a protective membrane which aids to hold the tumor together during mechanical handling and resection thereof, thereby significantly reducing tumor spillage and the danger of subsequent implantation metastases.

19 Claims, No Drawings

METHOD FOR RESECTION OF TUMORS

FIELD OF THE INVENTION

The present invention relates to a new method for resection of tumors by surgery.

BACKGROUND AND SUMMARY OF THE INVENTION

Malignant tumors located in the mucosa are very common throughout the population, and a vast majority of these tumors consist of so-called squamous cell carcinomas. The development of tumors in the mucosa is often promoted and/or caused by intake of carcinogenic substances, such as tobacco and alcohol. Furthermore, this type of tumors is often very aggressive and thus associated with a high mortality rate. Indeed, despite major advances in surgery, chemotherapy and radiation therapy, about 50% of the afflicted patients die from their cancer disease within a 5-year period after tumor diagnosis.

A vast majority of the tumors located in the mucosa are treated by surgery. However, such surgery is often technically complicated, and this is mainly a result of the general difficulty of access to these tumors. This is particularly the case if they are located in the throat or the oral cavity. Furthermore, a specific characteristic associated with tumors in the mucosa is a high abundance of newly developed tumors located on adjacent surfaces, including the surfaces of the respiratory tract. Indeed, such new tumors (known as "second primaries") are observed in about 10–20% of the patients within a 10-year period following a successful resection of the primary tumor.

Recent molecular biology research (see Worsham, M. J. et al., *Human Pathology*, 26(3), 251–261, 1995 and Bedi, G. C. et al., *Cancer Res.*, 56, 2484–2487, 1996) suggests that said second primaries are related to the primary tumor, and that they are in fact of the same monoclonal origin.

It is also known that the unavoidable mechanical handling of tumors during resection thereof often results in a tumor spillage, and detectable amounts of tumor cells have been observed on instruments and gloves used in surgery (see e.g. Curran, A. J., Smyth, D., Timon, C. V. I., "Reducing the risk of implantation of malignant cells intra-operatively", Abstract 401, 4th International Conference on Head and Neck Cancer, July 28–August 1, Toronto, CA, 1996). For inter alia this reason, it has for a long time been common practise during surgery to change both gloves and instruments before reconstructive surgery begins after the tumor has been resected.

In short, a likely explanation for the occurrence of said second primaries is that they are so-called implantation metastases resulting from tumor cells deposited and subsequently implanted on healthy tissue surfaces, whereby a new tumor is developed.

In summary, the occurrence of new tumors associated with resection of tumors, particularly of those located in the mucosa, is a problem which yet remains to be solved.

DISCLOSURE OF THE INVENTION

There is now provided a novel method for resection of tumors which overcomes the above-mentioned problem. According to the present invention, the tumor to be surgically removed is coated with a tissue adhesive composition before resection thereof. Thus, the tissue adhesive composition functions as a protective membrane which aids to hold the tumor together during mechanical handling and resection thereof, thereby significantly reducing the tumor spillage and danger of subsequent implantation metastases.

Accordingly, the present invention relates to a method for resection of a tumor, wherein said tumor is coated with a tissue adhesive composition, after which the coated tumor is resected. If the accessibility of the tumor so permits, said tissue adhesive composition is applied so that the entire exposed surface of the tumor becomes completely coated therewith. Apart from the application of the tissue adhesive composition in accordance with the present invention, the surgical procedure itself is performed entirely according to methodology known by a person skilled in the art.

Further, in an embodiment of the present invention, tissue adjacent to said tumor is coated with said tissue adhesive composition before the coated tumor is resected. All of the tissue adhesive composition applied to adjacent tissue is then removed at the same time as the coated tumor is resected.

During resection of e.g. a tumor in the oral cavity or throat, the mechanical stress exerted on the coated tumor can be rather high, since it is often subjected to both pressure and pulling forces. The properties of said tissue adhesive composition should therefore be such that it can both maintain its structural integrity and adhere to the tumor tissue during resection of the latter. Thus, in a preferred embodiment, said tissue adhesive composition is allowed to solidify and/or harden before the coated tumor is resected. Needless to say, the tissue adhesive composition should only be allowed to solidify and/or harden to such a degree that it is still flexible enough to be easily handled and removed together with the tumor coated therewith.

As an example, a suitable solidification may also involve a subsequent evaporation of a volatile, non-toxic solvent (e.g. water or an ethanol/water mixture) in which the tissue adhesive composition is dissolved, swelled or dispersed.

Furthermore, in order not to significantly impair the accessibility to the coated tumor and general ease of handling thereof during resection, the thickness of the applied tissue adhesive composition should preferably not exceed about 5 mm.

Typically, the tumors treated in accordance with the method of the present invention are located in the mucosa, particularly the mucosa of the oral cavity, oropharynx, nasopharynx, larynx, nasal cavity, paranasal sinuses, aerodigestive or gastrointestinal tract, vagina, cervix, uterus, bladder or the skin. Indeed, the present invention is particularly useful in such cases wherein said tumor is of epithelial origin, such as e.g. squamous cell carcinoma, adenocarcinoma and malignant melanoma, or is the result of non-epithelial tumors which have invaded the mucosa.

As examples of tissue adhesive compositions suitable for use in the present invention can be made of compositions based on alginic acid or a salt thereof, particularly sodium alginate. As for the latter, it will convert to its corresponding calcium salt upon contact with saliva. This conversion to a calcium salt initiates a hardening which in turn confers tissue adhering properties.

A two-component fibrin sealant known as Tisseel® Fibrin Sealant is available from Baxter Healthcare Corporation of Glendale, Calif., and may also be used, as it readily adheres to human mucosa. This product is a two-component tissue glue, which is readily applied even to large surfaces, after which it rapidly hardens to a jellylike state.

Furthermore, to a person skilled in the art, the properties and handling of any one of the above-mentioned compositions are well known. Depending on inter alia the particular location and texture of the tumor in question, a surgeon will readily adapt the application of the tissue adhesive composition (e.g. the amount and optional time for hardening thereof) to the particular circumstances.

As should be clear from the above disclosure, the present method provides a simple, rapid, efficient and cost-effective way of signficantly reducing the occurence of implantation metastases in general, albeit the present method is particularly useful in surgical resection of tumors located in the mucosa. It also deserves to be mentioned that the present method is applicable to both human and animal patients.

What is claimed is:

1. A method for resection of a tumor which has been identified as one needing resection comprising:
   at least partially coating said tumor with a tissue adhesive composition;
   after which the coated tumor is resected; and
   allowing said adhesive to hold said tumor together during handling thereof.

2. A method in accordance with claim 1 wherein:
   tissue adjacent to said tumor is substantially completely coated with said tissue adhesive composition before the coated tumor is resected.

3. A method in accordance with claim 2 wherein:
   said tissue adhesive composition is allowed to at least partially harden before the coated tumor is resected.

4. A method in accordance with claim 1 wherein:
   said tumor is located in mucosal tissue.

5. A method in accordance with claim 1 wherein:
   said tumor is located in skin.

6. A method in accordance with claim 1 wherein:
   said tumor is located in the oral cavity, oropharynx, nasopharynx, larynx, nasal cavity, paranasal sinuses, aerodigestive or gastrointestinal tract, vagina, cervix, uterus, bladder or skin.

7. A method in accordance with claim 1 wherein:
   said tumor is of epithelial origin or is the result of non-epithelial tumors which have invaded the mucosa.

8. A method in accordance with claim 7 wherein:
   said tumor is a squamous cell carcinoma, adenocarcinoma or malignant melanoma.

9. A method in accordance with claim 1 wherein:
   said tissue adhesive composition is based on alginic acid or a salt thereof.

10. A method in accordance with claim 9 wherein:
    said tissue adhesive composition is based on sodium alginate.

11. A method in accordance with claim 1 wherein:
    said tissue adhesive composition is two-component fibrin sealant known as Tisseel® Fibrin Sealant.

12. A method for resection of a tumor comprising:
    identifying and isolating said tumor in a subject;
    applying an adhesive composition to at least a portion of said tumor;
    said adhesive composition holding the tumor together during handling thereof;
    allowing said adhesive composition to at least partially harden;
    resecting said tumor; and
    keeping said adhesive composition in contact with said tumor until resection of said tumor is completed.

13. A method in accordance with claim 12 wherein:
    applying an adhesive composition to at least a portion of tissue adjacent to said tumor before the coated tumor is resected.

14. A method in accordance with claim 12 wherein:
    said tumor is located in mucosal tissue.

15. A method in accordance with claim 12 wherein:
    said tumor is located in skin.

16. A method in accordance with claim 12 wherein:
    said tumor is located at a location in said subject selected from the group consisting of: the oral cavity, oropharynx, nasopharynx, larynx, nasal cavity, paranasal sinuses, aerodigestive or gastrointestinal tract, vagina, cervix, uterus, bladder or skin.

17. A method in accordance with claim 12 wherein:
    said tumor is of epithelial origin or is the result of non-epithelial tumors which have invaded the mucosa.

18. A method in accordance with claim 17 wherein:
    said tumor is a squamous cell carcinoma, adenocarcinoma or malignant melanoma.

19. A method in accordance with claim 1 wherein:
    said tissue adhesive composition is selected from the group consisting of a composition based on alginic acid or a salt thereof, a tissue adhesive composition based on sodium alginate, or a two-component fibrin sealant known as Tisseel® Fibrin Sealant.

* * * * *